United States Patent [19]
Iwata et al.

[11] Patent Number: 5,506,225
[45] Date of Patent: Apr. 9, 1996

[54] ANTIBACTERIAL PENEM COMPOUNDS

[75] Inventors: Hiromitsu Iwata, Takatsuki; Takashi Nakatsuka, Osaka; Rie Tanaka, Ibaraki; Masaji Ishiguro, Takarazuka, all of Japan

[73] Assignee: Suntory Limited, Osaka, Japan

[21] Appl. No.: 971,828

[22] PCT Filed: Aug. 16, 1991

[86] PCT No.: PCT/JP91/01099

§ 371 Date: Feb. 19, 1993

§ 102(e) Date: Feb. 19, 1993

[87] PCT Pub. No.: WO92/03443

PCT Pub. Date: Mar. 5, 1992

[30] Foreign Application Priority Data

Aug. 20, 1990 [JP] Japan .................... 2-217053

[51] Int. Cl.$^6$ .................... C07D 499/00; A61K 31/43
[52] U.S. Cl. .................... 514/195; 514/192; 540/310
[58] Field of Search .................... 514/195, 190; 540/310; 519/192

[56] References Cited

U.S. PATENT DOCUMENTS

| | | | |
|---|---|---|---|
| 4,952,577 | 8/1990 | Alpegiani et al. | 540/310 |
| 4,997,829 | 5/1991 | Ishiguro et al. | 540/310 |
| 5,089,489 | 2/1992 | Alpegiani et al. | 540/310 |

FOREIGN PATENT DOCUMENTS

| | | |
|---|---|---|
| 0131374 | 1/1985 | European Pat. Off. . |
| 0199446 | 10/1986 | European Pat. Off. . |
| 0295100 | 12/1986 | European Pat. Off. . |
| 0275002 | 7/1988 | European Pat. Off. . |
| 0399228 | 11/1990 | European Pat. Off. . |
| 0410727 | 1/1991 | European Pat. Off. . |
| 2220203 | 1/1990 | United Kingdom . |

OTHER PUBLICATIONS

Bioreversible Carriers in Drug Design: Theory and Application, Pergamon Press, 1987, pp. 13–16, Hans Bundgaard, "Design of Bioreversible Drug Derivatives and The Utility of the Double Prodrug Concept".

The Journal of Antibiotics, vol. 41, No. 11, 1988, pp. 1685–1693, M. Ishiguro, et al., "Studies on Penem Antibiotics. 1. Synthesis and in Vitro Activity of Novel 2–Chiral Substituted Penems".

*Primary Examiner*—Nicholas Rizzo
*Attorney, Agent, or Firm*—Oblon, Spivak, McClelland, Maier, & Neustadt

[57] ABSTRACT

Antibiotic penem compounds are represented by the following formula:

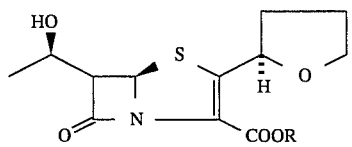

wherein R represents a physiological-hydrolyzable, ester-forming group. The physiologically hydrolyzable, ester-forming group useful in the penem compound of the present invention means a group which can be removed easily by in vivo hydrolysis, such as an acetyloxymethyl, 1-(acetyloxy)ethyl, pivaloyloxymethyl, 1-(ethoxycarbonyloxy)ethyl, 1-(isopropyloxycarbonyloxy)ethyl, 1-(cyclohexyloxycarbonyloxy)ethyl or 3-phthalidyl group. Antibiotic compositions for oral administration are also described.

10 Claims, No Drawings

ANTIBACTERIAL PENEM COMPOUNDS

TECHNICAL FIELD

The present invention relates to penem compounds, and more specifically to penem compounds which are expected to find clinical utility as promising antibiotics.

BACKGROUND ART

The present inventors previously found that a group of penem compounds represented by the following formula:

[Chemical structure of penem compound with HO, S, N, A, B, O, and COOR₁ groups]

wherein
R₁ is a hydrogen atom or allyl group,
—A— represents an oxygen or methylene group, and
—B— represents a methylene, ethylene or carbonyl group,
and their salts have excellent antibacterial activities on both gram-positive and gram-negative, aerobic or anaerobic bacteria (Japanese Patent Publication No. 207387/1986).

High safety of these compounds has been confirmed by safety test in which laboratory animals were used. Their development as medical drugs is now expected.

In the meantime, it has been found by the study on the correlation between structure and, antibacterial activities of these compounds [J. Antibiotics, 41, 1685 (1988)] that, among 2-substituents of penem, (R)-2-tetrahydrofuryl group provides the highest antibacterial activities while (S)-2-tetrahydrofuryl group, a diastereomer at its 2-side chain group, and (R) or (S)-3-tetrahydrofuryl group, a position isomer, provide weaker activities particularly against gram-negative bacteria.

For these reasons, compounds represented by the following formula (II):

[Chemical structure of compound (II) with HO, S, N, H, O, and COOR₂ groups]

wherein
R2 represents a hydrogen atom or a group capable of forming a pharmaceutically-acceptable salt,
have drawn interest as antibiotics. These compounds are also interested in that they do not require any special chemical modification for oral absorption and they themselves can be developed as both injections and oral drugs.

Namely, the bioavailability of the above-described compounds per se in laboratory animal (rats) has been found by no means inferior to commercial drugs which are used clinically.

However, from the viewpoint of safety and economy further enhancement of their bioavailability upon oral administration is apparently more advantageous. As far as the above compounds are concerned, there is still a room for further improvement in this regard.

Regarding improvements in the absorption upon oral administration, extensive studies have been conducted on penicillin and cephalosporin antibiotics so that many of these antibiotics are used as curative medicines. There are, however, only a few study reports of this type on penem and carbapenem antibiotics [J. Antibiotics, 36, 983, (1983); Japanese Patent Laid-Open No. 6728/1990]. It has therefore been interested in determining whether or not the approaches used for penicillin and cephalosporin antibiotics are equally applicable to penem compounds.

DISCLOSURE OF INVENTION

The present inventors have carried out an extensive investigation on the compounds (II) with a view toward making an improvement in their bioavailability. As a result, it has been found that protection of their carboxyl group with an ester-forming group which can be hydrolyzed easily in vivo can significantly improve their bioavailability, leading to the completion of the present invention.

The present invention provides a penem compound represented by the following formula (I):

[Chemical structure of compound (I) with HO, S, N, H, O, and COOR groups]

wherein
R represents certain physiologically-hydrolyzable, ester-forming group.

The physiologically hydrolyzable, ester-forming group useful in the penem compound of the present invention means a group which can be removed easily by in vivo hydrolysis. Examples include an acetyloxymethyl group, 1-(acetyloxy) ethyl group, pivaloyloxy-methyl group, 1-(ethoxycarbonyloxy) ethyl group, 1-(isopropyloxycarbonyloxy)ethyl group, 1-(cyclohexyloxycarbonyl)ethyl group and 3-phthalidyl group. When these groups contain an asymmetric carbon atom, it is preferable that they are optically active.

BEST MODE FOR CARRYING OUT THE INVENTION

The penem compound (I) of the present invention can be synthesized, for example, by reacting a halogenated alkyl compound (IV) with a penem compound (II') in accordance with the following formula:

[Chemical structures of compounds (II') and (IV) reacting with +RX to produce compound (I)]

wherein
X represents a halogen atom,
R₃ represents a hydrogen or alkali metal atom or an amino residuum, and
R has the same meaning as defined above.

When $R_3$ in the compound (II') is an alkali metal atom or an amino residuum in the above reaction, the target product can be obtained by stirring the compound (II') together with the halogenated alkyl compound (IV) in an organic solvent.

When $R_3$ in the compound (II') is a hydrogen atom on the other hand, it is first reacted with an alkali metal hydroxide, an alkali metal salt or an amine compound in an organic solvent to form a salt, and the mixture is then reacted with the halogenated alkyl compound (IV), whereby the target compound can be synthesized.

The halogenated alkyl compound represented by the formula (IV) can efficiently esterify the carboxyl group of the compound (II') with the group R to produce the target compound of the formula (I). Examples of the compound (IV) include those employed for the preparation of prodrugs of the penicillin or cephalosporin type.

Illustrated more specifically, they may be compounds of the formula (IV) in which R is a physiologically-hydrolyzable, ester-forming group such as an acetyloxymethyl group, 1-(acetyloxy) ethyl group, pivaloyloxymethyl group, 1-(ethoxycarbonyloxy)ethyl group, 1-(isopropyloxycarbonyloxy)ethyl group, 1-(cyclohexyloxycarbonyloxy)ethyl group or 3-phthalidyl group and X is a chlorine, bromine or iodine atom.

No particular limitation is imposed on the alkali metal insofar as it forms a salt with the compound (II'). Examples of the alkali metal include lithium, sodium and potassium. Examples of their hydroxides and salts include sodium hydroxide, potassium hydroxide, sodium bicarbonate, sodium carbonate, potassium bicarbonate and potassium carbonate. Exemplary amine compounds include ammonia, triethylamine, and diisopropylethylamine.

No particular limitation is imposed on the reaction solvent. Examples of the reaction solvent include aromatic hydrocarbons such as toluene and xylene, aliphatic hydrocarbons such as pentane and hexane, halogenated alkyls such as methylene chloride and chloroform, halogenated aryls such as chlorobenzenes, ketones such as acetone and methyl ethyl ketone, nitriles such as acetonitrile and propionitrile, amides such as dimethylformamide, sulfoxides such as dimethyl sulfoxide, ethers such as diethyl ether and tetrahydrofuran, and alcohols such as isopropanol and t-butanol. They can be used either singly or in combination.

The reaction may be carried out at room temperature or, in some instances, under heating below 80° C. The reaction time is generally 1–48 hours although it varies depending on the halogenated alkyl compound to be used.

The penem compound (I) obtained as a reaction product as described above may be used as is but, in general, is purified, as needed, by a method such as column chromatography or recrystallization for use as a medicine.

For oral, parenteral or external administration, the compounds according to the present invention can be formulated as antibiotics in a manner known per se in the art.

Although the dosage of each penem derivative of the present invention varies depending on many factors, the typical daily dosage ranges from 50 mg to 3 g for standard adults with the administration of 100 mg to 2 g in divided portions being preferred. In general, the above dosage will be administered in the form of a dosage unit which contains an appropriate amount of the active ingredient and a suitable, physiologically-acceptable carrier or extender.

For oral administration, tablets or capsules can be used. They may contain—together with the active ingredient—an extender, e.g., lactose, glucose, sucrose, mannitol, sorbitol or cellulose, and a lubricant, e.g., talc, stearic acid or a stearate salt. Tablets may additionally contain a binder, for example, hydroxypropyl cellulose or starch.

The compounds according to the present invention can be used not only for men but also for animals.

The present invention will hereinafter be described more specifically by the following examples. It should however be borne in mind that the present invention is not limited at all by these examples.

Example 1

Acetyloxymethyl (5R, 6S)-6-[(R)-1-hydroxyethyl]-2-[(R)-2-tetrahydrofuryl]penem-3-carboxylate (Compound 2):

To the mixture of sodium (5R,6S)-6-[(R)-1-hydroxyethyl]-2-[(R-2-tetrahydrofuryl) penem-3-carboxylate 2.5 hydrate (Compound 1, 3.52 g) and N,N-dimethylformamide (40 ml), the mixture of acetyloxymethyl bromide (1.84 g) and N,N-dimethylformamide (7 ml) was added dropwise under ice-cooling and stirring, followed by stirring at room temperature for a further 2 hours. The reaction mixture was then added with ethyl acetate (200 ml) and washed twice with water (200 ml). The ethyl acetate layer was dried and concentrated. The residue was separated and purified by passing it through a silica gel column, whereby 2.24 g of the title compound were obtained.

EXAMPLE 2

Phthalidyl (5R,6S)-6-[(R)-1-hydroxyethyl]-2-[(R)-2-tetrahydrofuryl)penem-3-carboxylate (Compound 8, Compound 9)

The mixture of sodium (5R,6S)-6-[(R)-1-hydroxyethyl]-2-[(R)-2-tetrahydrofuryl)penem-3-carboxylate 2.5 hydrate (Compound 1, 3 g), bromophthalide (3 g) and dimethyl sulfoxide (30 ml) was stirred at room temperature for 10 minutes. The reaction mixture was added with water, followed by extraction with ethyl acetate. The ethyl acetate layer was washed with water and the resulting organic layer was dried. Then, the solvent was diluted off. The residue thus obtained was separated and purified by passing it through a silica gel column, whereby the title compound was obtained. At that time, diastereomers relative to the asymmetric carbon atom of the phthalidyl group were separated. The less polar compound was designated as "Compound 8", while the more polar compound was designated as "Compound 9". The yields of those compounds were 1 g and 1.3 g, respectively.

EXAMPLE 3

1-(Cyclohexyloxycarbonyloxy)ethyl (5R,6S)-6-[(R)-1-hydroxyethyl]-2-[(R)-2-tetrahydrofuryl)penem-3-carboxylate (Compound 7):

Sodium (5R,6S)-6-[(R)-1-hydroxyethyl]-2-[(R)-2-tetrahydrofuryl)penem-3-carboxylate 2.5 hydrate (Compound 1, 3.52 g) was added to the mixture of 1-iodoethyl cyclohexylcarbonate (3.3 g) and N,N-dimethylformamide (60 ml), The resultant mixture was heated at room temperature for one hour, followed by the addition of ethyl acetate (300 ml). The reaction mixture thus obtained was washed with water. The ethyl acetate layer was dried and then concentrated. The residue was separated and purified by passing it through a silica gel column, whereby 1.38 g of the title compound was obtained.

EXAMPLES 4–7

In each example, sodium (5R,6S)-6-[(R)-1-hydroxyethyl]-2-[(R)-2-tetrahydrofuryl]penem-3-carboxylate 2.5 hydrate (Compound 1) and the corresponding halogenated alkyl compound, which is shown in Table 1, were processed in a similar manner to Example 3, whereby the penem compound of the present invention was obtained. Physical properties of the compounds obtained in each example are shown in Table 2.

TABLE 1

| Example No. | Comp'd No. | Starting halogenated alkyl compound | R | Reaction time (hr) | Yield (%) |
|---|---|---|---|---|---|
| 4 | 3 | $ICH(CH_3)OCOCH_3$ | $CH(CH_3)OCOCH_3$ | 5 | 37 |
| 5 | 4 | $ICH_2OCOC(CH_3)_3$ | $CH_2OCOC(CH_3)_3$ | 3 | 70 |
| 6 | 5 | $ICH(CH_3)OCOOC_2H_5$ | $CH(CH_3)OCOOC_2H_5$ | 3.5 | 50 |
| 7 | 6 | $ICH(CH_3)OCOOCH(CH_3)_2$ | $CH(CH_3)OCOOCH(CH_3)_2$ | 2 | 77 |

TABLE 2

| Comp'd No. | Compound | Appearance | $IR^{neat}$ ($cm^{-1}$) | NMR ($CDCl_3$) δ |
|---|---|---|---|---|
| 2 | Acetyloxymethyl (5R,6S)-6-[(R)-1-hydroxyethyl]-2-[(R)-2-tetrahydofuryl]penem-3-carboxylate | Colorless oil | 3486, 1788 1760, 1716 1573 | 1.34(3H, d, J=6Hz), 1.71–2.09(4H, m), 2.13(3H, S) 2.39–2.53(1H, m), 3.71(1H, d, J=6Hz), 3.80–3.91(1H, m), 3.91–4.02(1H, m), 4.14–4.27(1H, m), 5.32(1H, t, J=7Hz), 5.50(1H, d, J=1Hz), 5.81 & 5.86(each, 1H, d, J=6Hz) |
| 3 | 1-(Acetyloxy)ethyl (5R,6S)-6-[(R)-1-hyroxyethyl]-2-(R)-2-tetrahydrofuryl]penem-3-carboxylate | Yellow oil | 3458, 1786 1718 | 1.35(3/2H, d, J=6Hz), 1.35(3/2, d, J=7Hz), 1.53(3/2H, d, J=5Hz), 1.54(3/2H, d, J=5Hz), 1.73–2.12(4H, m), 2.08 (3H, d, J=6Hz), 2.37–2.54(1H, m), 3.71(1H, d, J=6Hz), 3.80–3.91(1H, m), 3.91–4.02(1H, m), 4.15–4.29(1H, m), 5.34(1H, t, J=7Hz), 5.50(1H, s), 6.89–6.98(1H, m) |
| 4 | Pivaloyloxymethyl (5R,6S)-6-[(R)-1-hydroxyethyl]-2-[(R)-2-tetrahydrofuryl]penem-3-carboxylate | Colorless oil | 3496, 1790 1753, 1720 1572 | 1.22(9H, s), 1.34(3H, d, J=6Hz), 1.70–2.05(4H, m), 2.37–2.52(1H, m), 3.71(1H, dd, J=1Hz, 6Hz), 3.80–3.91(1H, m), 3.91–4.02(1H, m), 4.15–4.28(1H, m), 5.31(1H, t, J=7Hz), 5.50(1H, d, J=1Hz), 5.82 & 4.89(each, 1H, d, J=5Hz) |
| 5 | 1-(Ethoxycarbonyloxy)ethyl (5R,6S)-6-[(R)-1-hydroxyethyl]-2-[(R)-2-tetrahydrofuryl]-penem-3-carboxylate | Colorless oil | 3450, 1789 1762, 1718 1570 | 1.27–1.39(6H, m), 1.58(3H, t, J=4Hz), 1.73–2.08(4H, m), 2.37–2.53(1H, m), 3.70(1H, d, J=6Hz), 3.79–3.91(1H, m) 3.91–4.04(1H, m), 4.15–4.30(3H, m), 5.29–5.39(1H, m) 5.49(1H, d, J–1Hz), 6.80–6.89(1H, m) |
| 6 | 1-(Isopropyloxycarbonyloxy)-ethyl (5R,6S)-6-[(R)-1-hydroxyethyl]-2-[(R)-2-tetrahydrofuryl]-penem-3-carboxylate | Colorless amorphous | 3450, 1790 1760, 1713 1573 | 1.28–1.40(9H, m), 1.48 & 1.59(each, 3/2H, d, J=4Hz), 1.75–2.09(4H, m), 2.38–2.54(1H, m), 3.70(1H, d, J=7Hz), 3.80–3.92 & 3.92–4.03(each, 1H, m), 4.15–4.29(1H, m), 4.85–5.00(1H, m), 5.29–5.40(1H, m), 5.49(1H, d, J=1Hz), 6.80–6.91(1H, m) |
| 7 | 1-(Cyclohexyloxycarbonyloxy)ethyl (5R,6S)-6-[(R)-1-hydroxyethyl]-2-[(R)-2-tetrahydrofuryl]penem-3-carboxylate | Colorless powder | 3400, 2938 1791, 1756 1258, 1076 | 1.30–1.38(3H), 1.35–2.00(6H, m), 2.40–2.55(1H, m) 3.68–3.71(1H, m), 3.80–4.03(2H, m), 4.18–4.28(1H, m), 4.60–4.73(1H, m), 5.30–5.38(1H, m), 5.49–5.50(1H, m), 6.80–6.88(1H, m) |
| 8 | Phthalidyl (5R,6S)-6-[(R)-1-hydroxyethyl]-2-[(R)-2-tetrahydrofuryl]penem-3-carboxylate (Low-polarity isomer) | Colorless crystals | 3300, 2359 1784, 1717 972 | 1.30(3H, d, J=6Hz), 1.75–1.90(1H, m), 1.95–2.05(2H, m), 2.45–2.55(1H, m), 3.71(1H, dd, J=1Hz, 6Hz), 3.85–4.05 (2H, m), 4.10–4.20(1H, m), 5.42(1H, t, J=7Hz), 5.48 (1H, d, J–1Hz), 7.41(1H, s), 7.60–7.68(1H, m), 7.72–7.78 (2H, m), 7.91(1H, d, J=7Hz) |
| 9 | Phthalidyl (5R,6S)-6-[(R)-1-hydroxyethyl]-2-[(R)-2-tetrahydrofuryl]penem-3-carboxylate (High-polarity isomer) | Colorless amorphous | 3300, 1784 1717, 971 | 1.34(3H, d, J=6Hz), 1.75–2.05(3H, m), 2.20–2.35(1H, m), 3.72(1H, dd, J=1Hz, 6Hz), 3.75–3.80(1H, m), 3.96–4.00 (1H, m), 4.15–4.25(1H, m), 5.14(1H, t, J=6Hz), 5.50 (1H, d, J=1Hz), 7.48(1H, s), 7.65–7.80(3H, m), 7.94 (1H, d, J=5Hz) |

The bioavailability of certain compounds (I) of the present invention was tested relying upon their recovery rates in urine.

Each test compound (30 μmole/kg) was orally administered to SD strain rats (three male rats per group). Urine was collected over 6 hours from the administration, and the recovery rate of the corresponding compound present in the urine was determined by bioassay. The results are shown below.

TABLE 3

| Comp'd No. | R in the compound (I) | urinary recovery (%) | Ratio to Control |
|---|---|---|---|
| 1 | —Na | 4.38 | 1 |

TABLE 3-continued

| Comp'd No. | R in the compound (I) | urinary recovery (%) | Ratio to Control |
|---|---|---|---|
| (Control) | | | |
| 2 | $-CH_2OCOCH_3$ | 25.05 | 5.7 |
| 3 | $-CH(CH_3)OCOCH_3$ | 12.31 | 2.8 |
| 4 | $-CH_2OCOC(CH_3)_3$ | 13.54 | 3.1 |
| 5 | $-CH(CH_3)OCOOC_2H_5$ | 23.47 | 5.4 |
| 6 | $-CH(CH_3)OCOOCH(CH_3)_2$ | 26.09 | 6.0 |
| 7 | $-CH(CH_3)OCOOC_6H_{11}$ | 4.58 | 1.0 |

TABLE 3-continued

| Comp'd No. | R in the compound (I) | urinary recovery (%) | Ratio to Control |
|---|---|---|---|
| 8 | 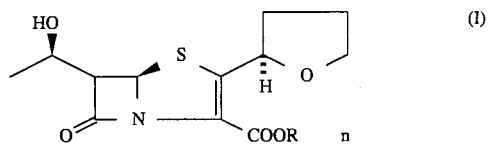<br>(Low polar isomer) | 16.76 | 3.8 |
| 9 | 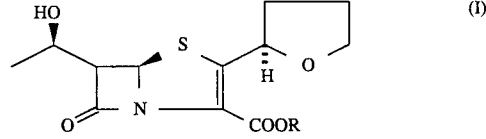<br>(High polar isomer) | 14.20 | 3.2 |

As is apparent from the results, the compounds (I) of the present invention showed the higher urinary recovery rates compared with the penem compound (II). This indicates that the bioavailability has been significantly improved by the esterification of the carboxyl group of the penem compound (II) with the ester-forming groups in accordance with the present invention.

Preparation Examples

In each of the following preparation examples., the active ingredient may be, for example, Compound 6 or an equivalent amount of any one of the other compounds of the present invention.

| | Preparation 1 Capsules | |
|---|---|---|
| Ingredient No. | Ingredient | mg/capsule |
| 1 | Invention compound | 150 |
| 2 | Lactose | 20 |
| 3 | Magnesium stearate | 4 |
| | (Total) | 174 mg |

(Production procedures)

Ingredients 1 and 2 were combined together in a suitable mixer, to which Ingredient 3 was added, followed by further mixing. The resultant mixture was filled into capsules using a capsule filling machine.

| | Preparation 2 Tablets | |
|---|---|---|
| Ingredient No. | Ingredient | mg/tablet |
| 1 | Invention compound | 150 |
| 2 | Crystalline cellulose | 50 |
| 3 | calcium carboxymethylcellulose | 10 |
| 4 | Magnesium stearate | 4 |
| | (Total) | 214 mg |

(Production procedures)

Ingredients 1–3 were combined together in a suitable mixer, to which Ingredient 4 was added, followed by mixing for additional several minutes. The resultant mixture was compressed into tablets of a predetermined size and weight by a tableting machine.

Industrial Applicability

As has been described above, the compounds of the present invention exhibit excellent bioavailability so that they can be advantageously used as oral antibiotics.

We claim:

1. A penem compound represented by the following formula (I):

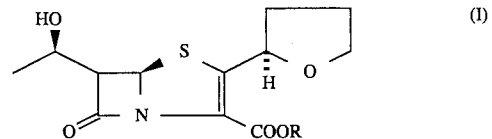

wherein R represents an acetyloxymethyl group, a 1-(ethoxycarbonyloxy)ethyl group or a 1-(isopropyloxycarbonyloxy)ethyl group.

2. The compound of claim 1, wherein R represents an acetyloxymethyl group.

3. The compound of claim 1, wherein R represents a 1-(ethoxycarbonyloxy)ethyl group.

4. The compound of claim 1, wherein R represents a 1-(isopropyloxycarbonyloxy)ethyl group.

5. An antibiotic composition comprising an effective amount of a compound of the following formula (I):

wherein R represented an acetyloxymethyl group, a 1-(ethoxycarbonyl)ethyl group or a 1-(isopropyloxycarbonyloxy)ethyl group, in admixture with a pharmaceutically-acceptable carrier.

6. The composition of claim 5, wherein R represents an acetyloxymethyl group.

7. The composition of claim 5, wherein R represents a 1-(ethoxycarbonyloxy)ethyl group.

8. The composition of claim 5, wherein R represents a 1-(isopropyloxycarbonyloxy)ethyl group.

9. A method of treating an infectious disease in a subject which comprises administering to the subject an effective amount of a penem compound represented by the following formula (I):

wherein R represents an acetyloxymethyl group, a 1-(ethoxycarbonyloxy)ethyl group or a 1-(isopropyloxycarbonyloxy)ethyl group.

10. The method of claim 9, wherein the penem compound is administered orally.

* * * * *